US00PP16352P3

(12) United States Plant Patent
Knudsen

(10) Patent No.: US PP16,352 P3
(45) Date of Patent: Mar. 21, 2006

(54) ***DAHLIA* PLANT NAMED 'MAURITIUS'**

(50) Latin Name: ***Dahlia* (hybrid)**
Varietal Denomination: Mauritius

(75) Inventor: Jan Skjold Knudsen, Odense N (DK)

(73) Assignee: Dalina APs, Odense N (DK)

( * ) Notice: Subject to any disclaimer, the term of this patent is extended or adjusted under 35 U.S.C. 154(b) by 101 days.

(21) Appl. No.: 10/808,379

(22) Filed: Mar. 25, 2004

(65) Prior Publication Data

US 2005/0216996 P1 Sep. 29, 2005

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—Foley & Lardner, LLP

(57) ABSTRACT

A new and distinct cultivar of *Dahlia* plant named 'Mauritius' characterized by its red-purple ray floret color, RHS 65A, yellow base 5C; leaf length up to 16 cm; leaf width 14 cm compact plant habit; and vigorous growth habit.

3 Drawing Sheets

Genus and species of the plant claimed: *Dahlia* (hybrid). Variety denomination: 'Mauritius'.

BACKGROUND OF THE INVENTION

The present Invention relates to a new and distinct cultivar of *Dahlia* plant, botanically known as *Dahlia* (hybrid), and hereinafter referred to by the name 'Mauritius'. The new cultivar 'Mauritius' is a product of a planned breeding program and was selected by the Inventor, Jan Skjold Knudsen, in Fyn, Denmark. The new cultivar 'Mauritius' originated from a cross made by the Inventor between the *Dahlia* cultivar designated 'Anne' (unpatented) as the female parent and the *Dahlia* cultivar designated '00.D.031' (unpatented) as the male parent.

Asexual reproduction by cuttings of the new variety in Fyn, Denmark has demonstrated that the combination of characteristics as described herein for 'Mauritius' are firmly fixed and are retained through successive generations of asexual reproduction. The new variety reproduces true to type.

BRIEF DESCRIPTION OF THE INVENTION

'Mauritius' has not been tested under all available environmental conditions and the phenotype may vary with variations in environmental conditions such as temperature, light intensity, day length and humidity, without a change in genotype of the plant.

The following traits have been repeatedly observed and are determined to be the unique characteristic of 'Mauritius'. The following characteristics in combination distinguish 'Mauritius' as a new and distinct cultivar:

1. Red-purple ray floret color, RHS 65A, yellow base 5C;
2. Leaf length up to 16 cm; leaf width 14 cm;
3. Compact plant habit; and
4. Vigorous growth habit.

Side-by-side comparisons between the new *Dahlia* cultivar 'Mauritius' and the parental cultivars, 'Anne' and '00.D.031', were conducted by the Inventor in Fyn, Denmark. 'Anne' has about half the number of inflorescences and buds per plant in comparison to 'Mauritius'. 'Mauritius' differs from the male parental cultivar, '00.D.031', primarily in ray floret color and inflorescence size. The ray florets of 'Mauritius' are red-purple, whereas the ray florets of '00.D.031' are white. The inflorescence of '00.D.031' is also smaller in size than 'Mauritius'.

Of the commercial cultivars known to the Inventor, the most similar in comparison to the new *Dahlia* cultivar 'Mauritius' is the female parental cultivar, 'Anne'.

BRIEF DESCRIPTION OF THE DRAWINGS

The accompanying color photographs illustrate the overall appearance and details of inflorescence form color and structures of the new cultivar, showing the colors as true as it is reasonably possible to obtain in color reproductions of this type. Colors in the photographs may differ slightly from the color values cited in the detailed botanical description, which accurately describe the actual colors of the new *Dahlia*.

The first photograph is a side view of a typical flowering plant of 'Mauritius' as grown in an 11 cm pot.

The second photograph is a top view of a typical flowering plant of 'Mauritius'.

The third photograph is a close-up of the inflorescence of 'Mauritius'.

DETAILED BOTANICAL DESCRIPTION

The following observations, measurements and values describe 8 week old plants grown under commercial conditions. Plants described were grown in a greenhouse in Fyn, Denmark with average day temperatures of 18° C. to 25° C., and night temperature of 16° C. All color references are measured against The Royal Horticultural Society (R.H.S.) Colour Chart. Colors are approximate as color depends on horticultural practices such as light level and treatment rate, among others, without however any variance in genotype.

Plant:

*Form.*—Globular, upright.

*Height.*—20 cm.

*Spread.*—20 cm.
*Natural flowering season.*—Summer to fall.
*Crop time.*—After rooting, about 10–12 weeks are required to produce finished flowering plants in 11 cm pots.
*Plant vigor.*—Vigorous.
*Root structure.*—Fibrous.
*Stem.*—Yellow-green RHS 144, glabrous; diameter 12 mm.
*Lateral branches.*—12 in quantity; 7–10 mm diameter; 14 cm in length (including inflorescence); color: yellow-green, RHS 144C.
*Internode length.*—3 cm.

Foliage:
*Leaves.*—Quantity: 4–5 pairs per lateral branch. Arrangement: Opposite, decussate. Length: Up to 16 cm. Width: 14 cm. Shape: Elliptical, acuminate tip, decurrent base, crenate margin. Texture: Glabrous. Color: Upper side: green RHS 137 A (both mature and immature); underside gray-green RHS 191 C (immature), RHS 191B (mature).
*Compound leaves.*—None. Vein color: Upper side 138C; under side yellow-green RHS 144B. Petiole: 2–3 cm in length; 5–8 mm diameter; color RHS 144A.

Inflorescence:
*Arrangement.*—Composite inflorescences in leaf axils.
*Inflorescence type.*—Capitulum.
*Inflorescence height.*—3–4 cm.
*Inflorescence width.*—7–8 cm.
*Flowering habit.*—Upright.
*Quantity of inflorescences.*—2–3 per lateral stem.
*Inflorescence longevity.*—7 days on the plant.

Bud:
*Quantity.*—2–3 per lateral stem (buds continue to develop when dead inflorescences are removed).
*Shape.*—Globular.
*Size.*—Up to 2 cm in length, 1 cm diameter.
*Color.*—RHS 144C.

Florets:
*Appearance.*—Disc: tubular to single, floret (5–7 whorls of disc florets, each with 1 to 20 florets to equal a total of about 60 disc florets, which are yellow in appearance due to the transparent corollas and the underplaying yellow, RHS 11A; ray: single fused floret (7 whorls of ray florets, each with 1 to 18 florets to equal a total of about 70 ray florets).
*Shape.*—Disc, lanceolate; ray oval, slightly involute.
*Number.*—About 60 disc florets and 70 ray florets per capitulum (depending on light and temperature conditions).
*Length.*—Disc 2–5 mm, ray 25 mm.
*Width.*—Disc 2 mm, ray 19 mm.
*Diameter.*—Disc 2–3 mm.
*Margin.*—(Disc and ray), entire.
*Apex.*—(Disc and ray), rounded.
*Color.*—Disc: translucent showing yellow, RHS 11A, anthers; Ray: immature upper side, red-purple RHS 68C with yellow base, RHS 5D; immature under side, light red-purple RHS 69B at base and purple, RHS 76D, apically; mature upper side, red-purple RHS 65A, with yellow base RHS 5C; mature under side red purple RHS 65D (development and tones of color for florets may change slightly depending on light and temperature conditions).

Phyllaries:
*Length.*—14 mm.
*Width.*—9 mm.
*Margin.*—Entire.
*Base.*—Fused.
*Apex.*—Rounded.
*Color.*—Immature upper side RHS 138A; immature under side RHS 143D with stripes RHS 143A; mature upper side RHS 137A; under side RHS 191B with stripes RHS 143A.

Calyx: 2 mm length, 1.5 cm diameter.

Peduncle: 8 cm length, 3 mm diameter; strength: strong; color RHS 144C with stripes RHS 144A.

Reproductive organs:

Androecium:
*Location.*—Disc florets only.
*Anthers.*—4 mm in length, RHS 23B.
*Pollen.*—RHS 14A.

Gynoecium:
*Location.*—Disc florets only.
*Pistils.*—1 per disc floret, 15 mm length.
*Stigma.*—RHS 14A.
*Style.*—10 mm length, RHS 1B.
*Ovary.*—RHS 150B.

Temperature tolerance: High tolerance to 35° C.; low tolerance to 0° C.

I claim:

1. A new and distinct cultivar of *Dahlia* plant named 'Mauritius', as described and illustrated herein.

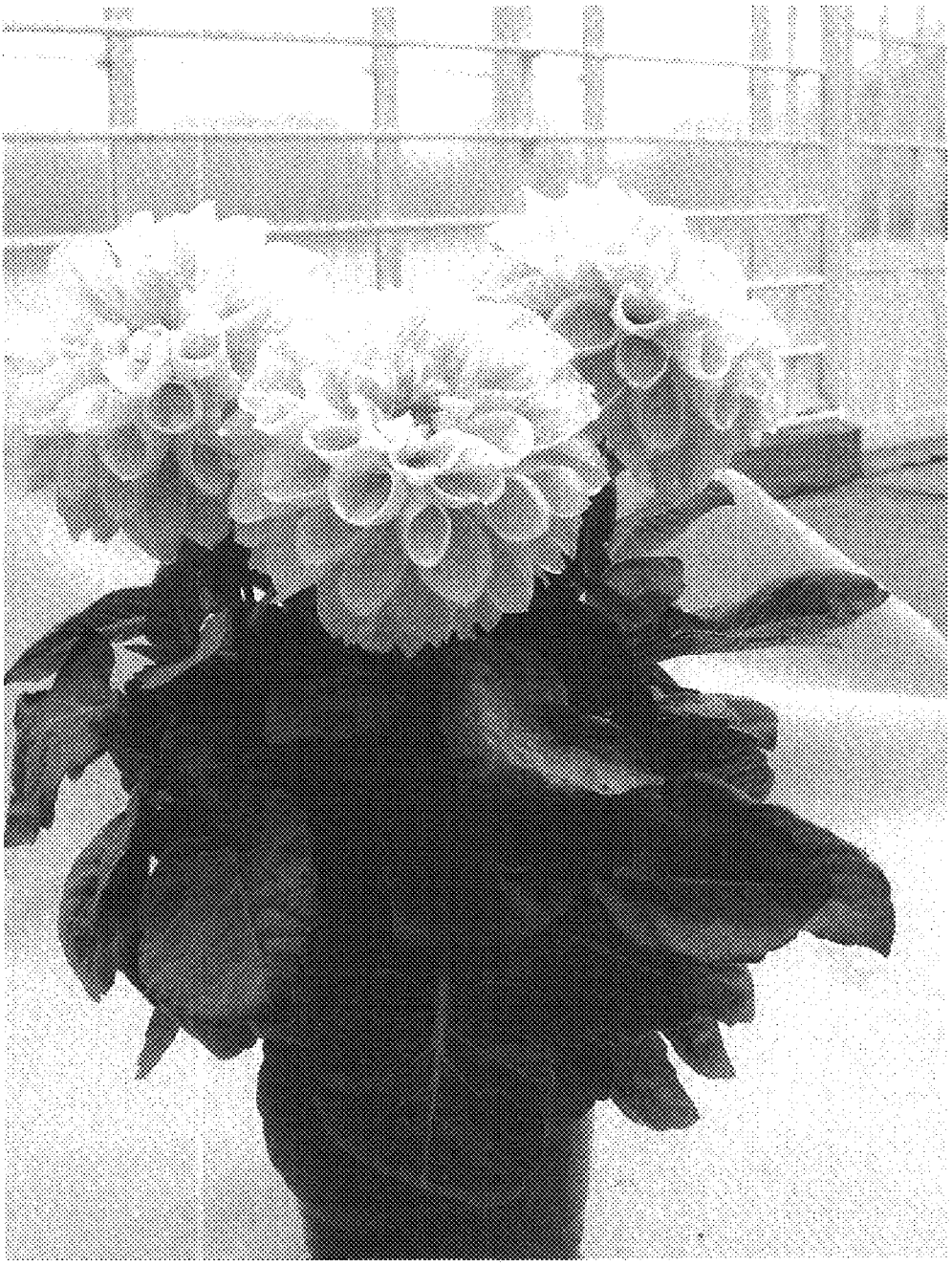

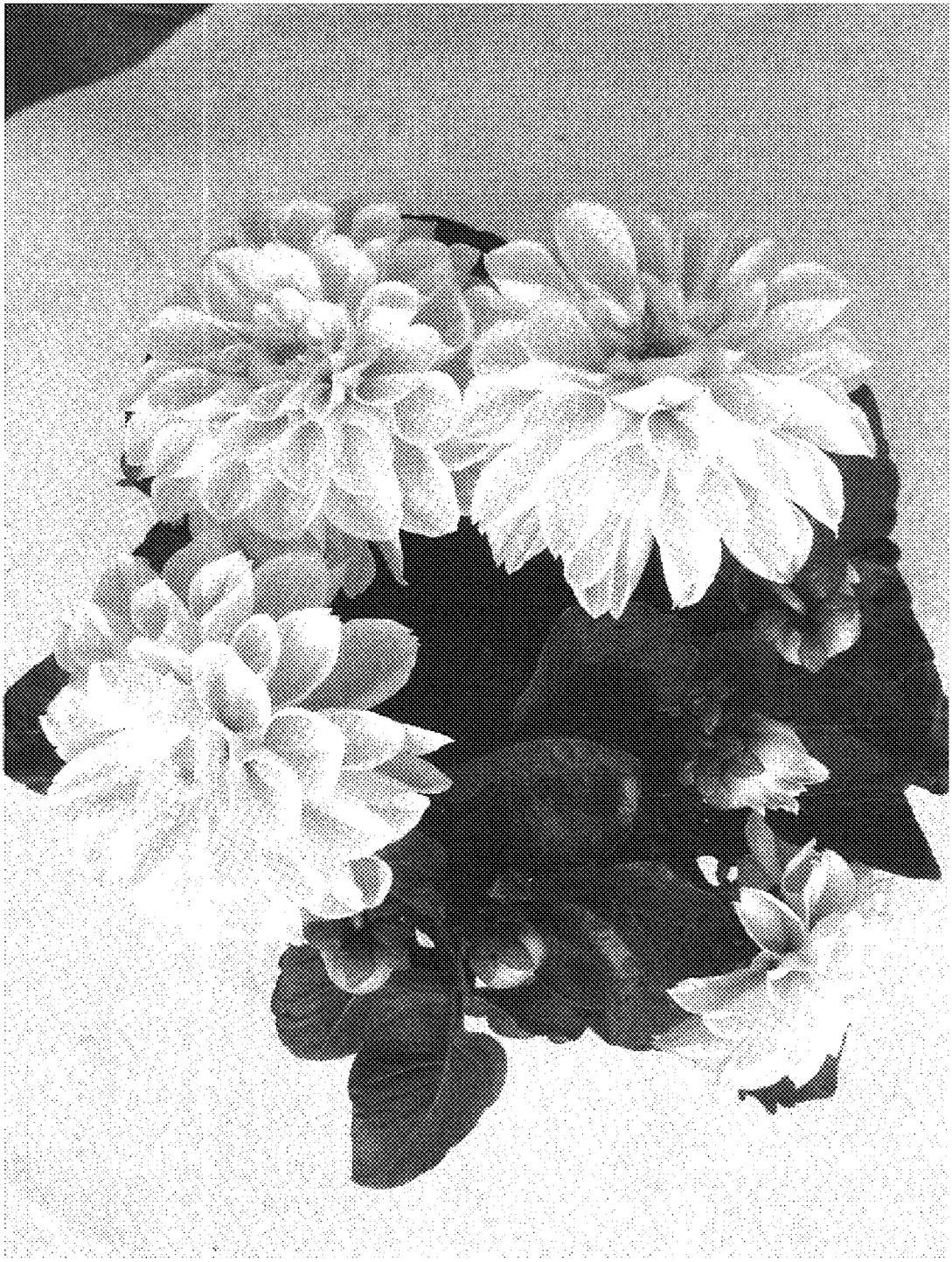

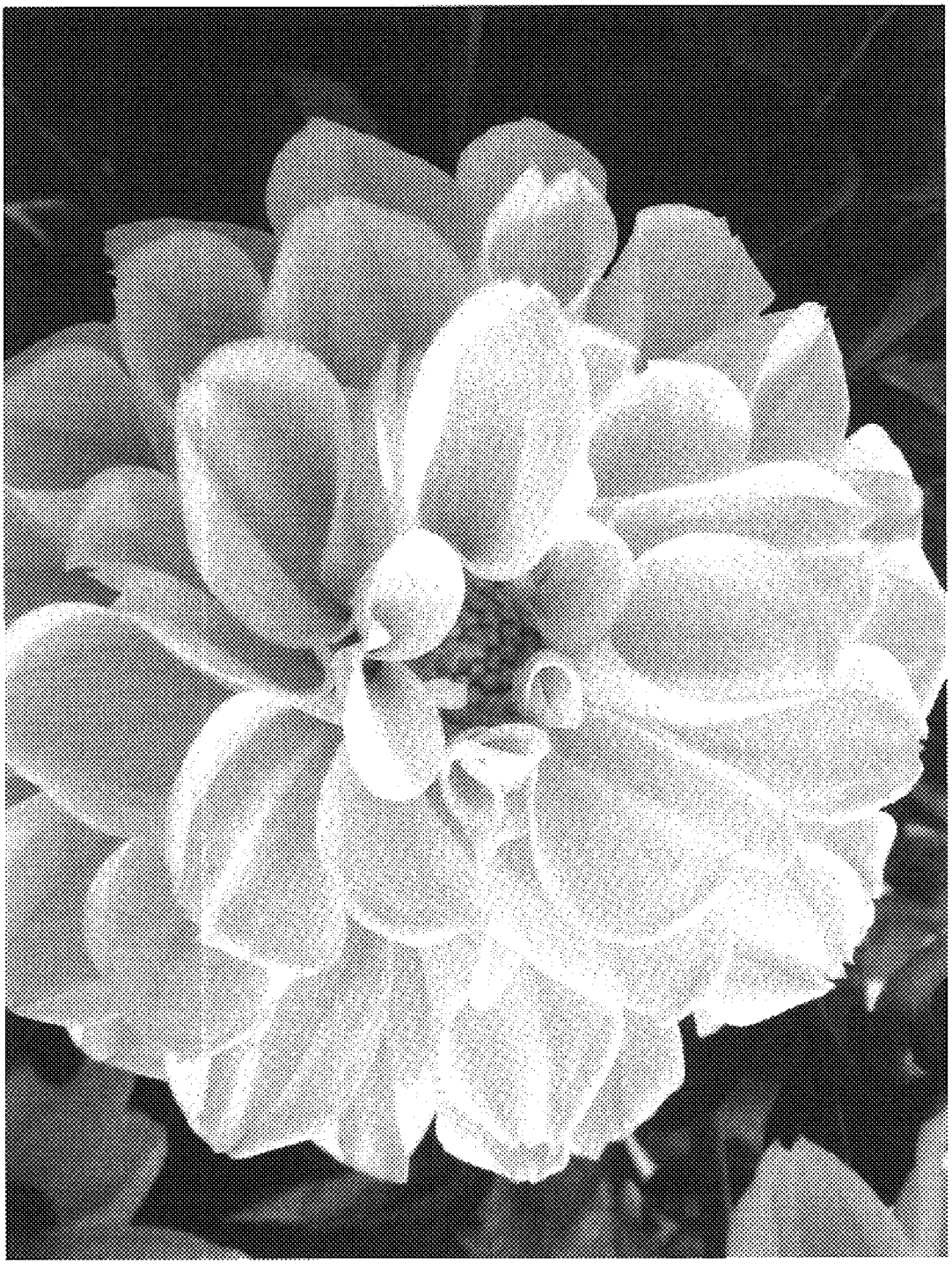

* * * * *